United States Patent [19]

Heffels

[11] Patent Number: 5,764,358
[45] Date of Patent: Jun. 9, 1998

US005764358A

[54] METHOD AND APPARATUS FOR DETERMINING THE SHAPE CHARACTERISTICS OF PARTICLES

[75] Inventor: Camiel Marie Godfried Heffels, Deidesheim, Germany

[73] Assignees: Technische Universiteit Delft, Delft; Stichting Voor de Technische Wetenschappen, Utrecht, both of Netherlands

[21] Appl. No.: 602,731

[22] PCT Filed: Aug. 9, 1994

[86] PCT No.: PCT/NL94/00188

§ 371 Date: Apr. 16, 1996

§ 102(e) Date: Apr. 16, 1996

[87] PCT Pub. No.: WO95/06238

PCT Pub. Date: Mar. 2, 1995

[30] Foreign Application Priority Data

Aug. 20, 1993 [NL] Netherlands ............... 9301446

[51] Int. Cl.⁶ .................................. G01N 21/00
[52] U.S. Cl. ................ 356/336; 356/338; 356/343
[58] Field of Search ................. 356/335–338, 356/343; 250/208.1, 208.6, 237 G; 359/566, 569

[56] References Cited

U.S. PATENT DOCUMENTS

| | | | |
|---|---|---|---|
| 4,070,113 | 1/1978 | Frazer et al. | 356/343 |
| 4,173,415 | 11/1979 | Wyatt | 356/343 |
| 4,263,508 | 4/1981 | Leary et al. | 356/335 |
| 4,274,741 | 6/1981 | Cornillault | 356/336 |
| 4,871,251 | 10/1989 | Preikschat et al. | 356/336 |
| 4,890,920 | 1/1990 | Niziolek et al. | 356/336 |
| 4,927,268 | 5/1990 | Carr et al. | 356/338 |
| 5,007,737 | 4/1991 | Hirlemann, Jr. | 356/336 |
| 5,089,714 | 2/1992 | Ludlow et al. | 356/343 |
| 5,101,113 | 3/1992 | Hirlemann, Jr. | 356/336 |
| 5,164,787 | 11/1992 | Igushi et al. | 356/336 |
| 5,185,641 | 2/1993 | Igushi et al. | 356/336 |
| 5,315,115 | 5/1994 | Gerber | 356/336 |
| 5,379,113 | 1/1995 | Niwa | 356/336 |
| 5,400,139 | 3/1995 | Shimaoka | 356/336 |

FOREIGN PATENT DOCUMENTS

| | | |
|---|---|---|
| 2 204 678 | 11/1988 | United Kingdom. |
| WO 90/10216 | 9/1990 | WIPO. |
| WO 91/10123 | 7/1991 | WIPO. |

OTHER PUBLICATIONS

A. Boxman et al., "Deconvolution of light-scattering patterns by observing intensity fluctuations", Applied Optics, Nov. 20, 1991, vol. 30, No. 33, pp. 4818–4823.

G. Grehan et al., "Comparison of the diffraction theory and the generalized Lorenz–Mie theory for a sphere arbitrarily located into a laser beam", Optics Communications, 1992, vol. 90, pp. 1–6.

*Primary Examiner*—Frank G. Font
*Assistant Examiner*—Jason D. Vierra-Eisenberg
*Attorney, Agent, or Firm*—Young & Thompson

[57] ABSTRACT

A method and apparatus determines the shape characteristics of articles flowing through a transparent cell through which a light beam is projected. The intensity of light scattered by the particles is measured with a detector which has one or more concentric rings or parts of rings, at least one of which is provided with one or more isolated segments. The rings and the isolated segments are coupled to an energy meter, signal amplitudes therefrom are statistically processed to provide amplitude classes. The shape characteristics of the particles are determined from a graphical or numerical comparison of the amplitude classes.

10 Claims, 4 Drawing Sheets

METHOD AND APPARATUS FOR DETERMINING THE SHAPE CHARACTERISTICS OF PARTICLES

BACKGROUND OF THE INVENTION

The invention firstly relates to a method for detecting the shape characteristics of particles.

It is known to determine the particle size distribution by means of light scattering. With this procedure a laser beam is directed through a transparent cell containing particles flowing therein and the intensity of the light scattered by the particles is determined with the aid of a photodetector array comprising a number of concentric rings or parts of rings which are coupled to an energy meter. The photodetector is a disc made of semiconductor material and the rings are formed by etching dividing lines on the semiconductor material and thus isolating the rings from one another.

The light intensity fluctuations can be processed statistically and the results (for example graphical results) thereof are an indication of the size distribution of the particles. Reference is made to the article in the journal Applied Optics. vol. 30. pp. 4818–4823. 1991 entitled Deconvolution of Lights Scattering Patterns by Observing Intensity Fluctuations. the authors of which are A. Boxman. H. G. Merkus. P. J. T. Verheijen and B. Scarlett.

However. information on the shape of the particles can also be derived from the fluctuation in the light intensity of light scattered be particles. The particle size is used as a control parameter in a number of individual processes and in various of these processes the shape of the particles is equally as important as, and possibly more important than, the size of the particles alone. Examples are grinding processes and industrial crystallisation processes. in which agglomeration. mutual abrasion of the particles and the effect of additives are of importance for the crystal shape.

Because signal fluctuations originating from a detector element are dependent not only on the number of particles but also on the shape of the particles. particle shape will also have to be taken into account when determining the particle size distribution in the case of particles which can change in shape.

SUMMARY OF THE INVENTION

The aim of the invention is. now. to provide a method for determining the shape characteristics of particles using apparatus which is largely known for determination of the particle size distribution.

According to the invention. the method is. to this end. characterised in that a light beam is directed onto a transparent cell containing particles flowing therein and the intensity of the light scattered by the particles is measured with the aid of a photodetector array or a mask containing programmable light valves comprising one or more concentric rings or parts of rings. at least one of which is provided with one or more isolated segments, the rings and isolated segments being coupled to an energy meter, the signal amplitudes of which are statistically processed to give amplitude classes. and the shape characteristics are determined from graphical or numerical comparison of said amplitude classes.

The amplitude of the signals from one or more rings and the amplitude of the signals from one or more isolated segments can be processed to produce an amplitude frequency distribution plot, the shape characteristics being determined from the difference in amplitude frequency distribution of signals originating from the ring or rings and signals originating from the isolated segment or isolated segments.

Another option is that the amplitude of the signals from a number of isolated segments of one ring are processed to produce a correlation plot and the shape characteristics are determined from the shape of this plot. This option had the advantage that the shape characteristics can be expressed in a characteristic angle spectrum.

The invention also relates to an apparatus for determining the shape characteristics of particles. An apparatus which comprises a light source or laser source for generating a light beam or laser beam. a transparent cell through which particles can be passed. a photodetector array or mask containing programmable light valves comprising one or more rings which are coupled to an energy meter, and computing means for statistical processing of signal amplitudes to produce amplitude classes is known per se. The novel features are that segments are isolated on at least one of the rings. which isolated segments are coupled to the energy meter, and that the computing means are able to process the amplitudes originating from signals from the rings and originating from signals from the isolated segments to produce amplitude classes and to calculate correlation coefficients.

Finally. the invention relates to a photodetector or a programmable mask. It is known that the photodetector has a number of concentric rings or parts of rings. it being possible to couple each ring to an energy meter. A mask involves a number of concentric programmable light valves. in the form of rings or parts of rings. through which the light beam coupled to an energy meter. is measured, as described in U.S. Pat. No. 4,735,487 and DE-A-3538413. In both cases it is necessary according to the invention that one or more segments are isolated on at least one of the rings or parts of rings. which segments can likewise be coupled to the energy meter.

BRIEF DESCRIPTION OF THE DRAWINGS

The invention will now be explained in more detail with the aid of the figures.

DESCRIPTION OF THE PREFERRED EMBODIMENTS

Figure 1:
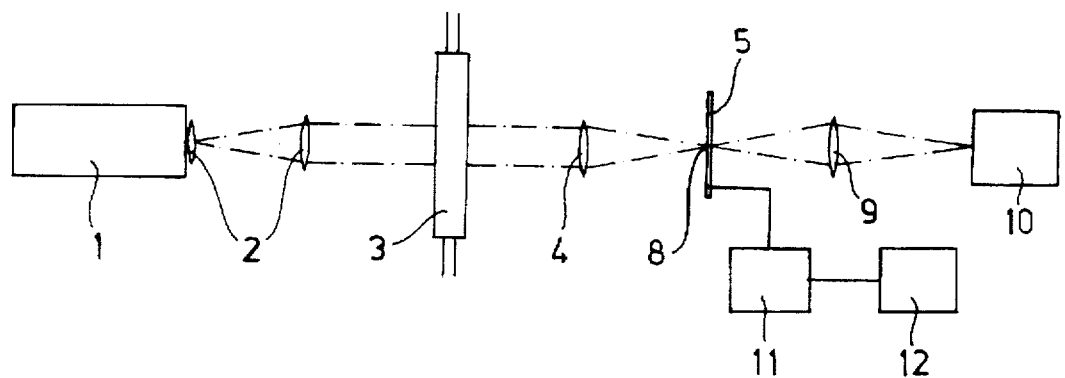
FIG. 1 shows a diagrammatic representation of a laser diffraction apparatus to be used with the method according to the invention.
Figure 2:
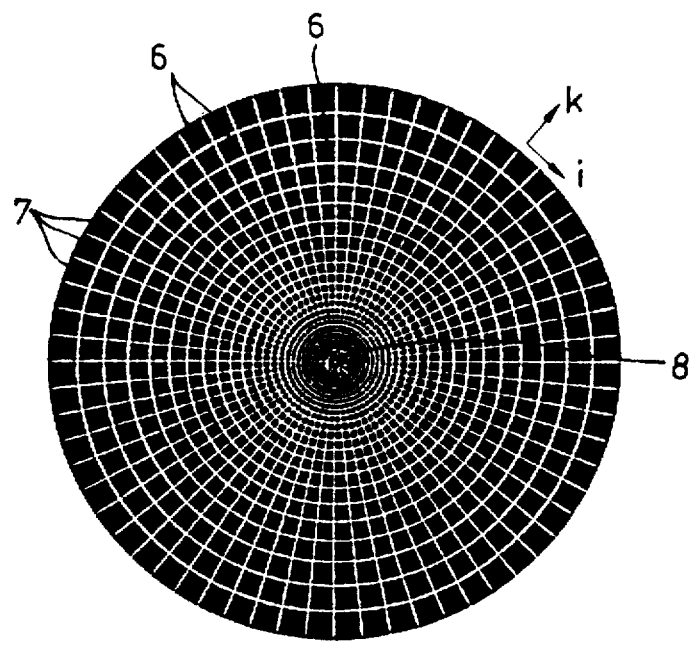
FIG. 2 shows a view of a photodetector used in the apparatus according to FIG. 1.

An apparatus shown in FIG. 1 comprises a laser 1 which. via a "beam expander" 2. throws a laser beam onto a transparent optical cell 3 through which particles which have to be subjected to shape determination are flowing. The light scattered by the particles is focused by a Fourier lens 4 onto a photo diode detector 5 which is positioned at a distance from the Fourier lens 4 equal to the focal length of the latter. As FIG. 2 shows, the detector 5 comprises a disc which is made up of a number of concentric rings 6 (for example 32), each ring being subdivided into a number of wedge-shaped sections 7 (for example 64). The rings 6, like the wedge-shaped sections 7, are separate from one another. A hole 8 is present in the centre of the detector disc. The light passing through this hole is fed via a lane 9 to an obscuration detector 10. The optical cell 3 can also be placed between the photodetector and the Fourier lens 4; this is known as the Reverse Fourier arrangement.

Each of the rings 6 and each of the wedge-shaped sections 7 is coupled to an energy meter 11 which measures the energy emitted by a ring or wedge-shaped section and transmits the associated energy amplitude signals to a computer 12 for statistical processing.

The rings 6 give signals from which the radial intensity distribution is determined and the wedge-shaped sections 7 give signals from which azimuthal fluctuations can be derived.

A signal $L_i^k$ from the disc originated from a wedge-shaped section having number i which is located on a ring having number k.

Figure 3:
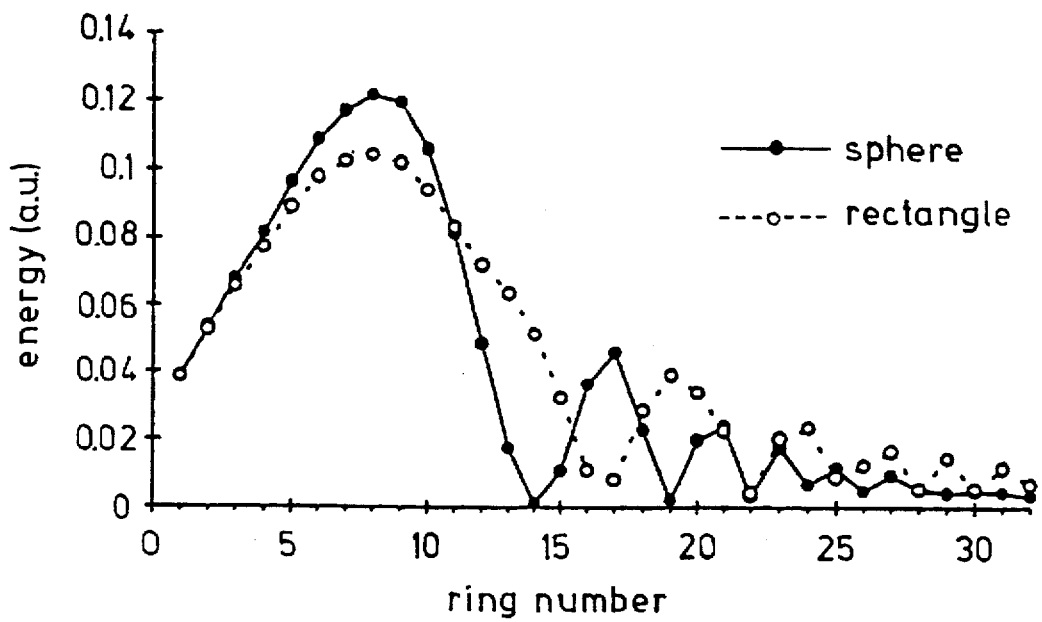
FIG. 3 shows a plot of the signal energy as a function of the ring numbers for both spherical and block-shaped particles of equal size.

FIG. 3 is a plot showing the relationship between the ring number and the energy amplitude for spherical particles and block-shaped particles.

Figure 4:
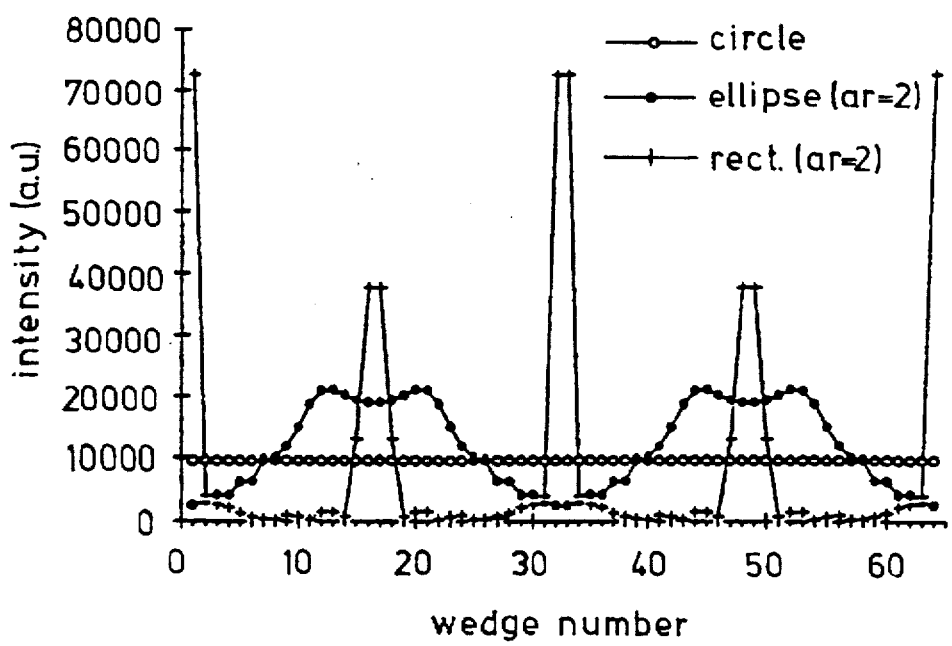
FIG. 4 shows a plot of the signal energy as a function of the number of the wedge-shaped section on a ring for. successively. a single spherical particle. a single ellipsoidal particle and a single block-shaped particle.

FIG. 4 is a plot showing the relationship between the wedge number and the energy amplitude for spherical particles, ellipsoidal particles and block-shaped particles for a fixed direction of orientation on the largest ring.

Particles having very diverse directions of orientation flow simultaneously through the cell 3. The signal from a wedge-shaped section for a set of particles is a linear combination of the wedge signals from a single particle. The signal fluctuations originating from a single detector element depend not only on the statistical number of particles in the cell 3 but also on the shape of the particles. The signal variation originating from a single wedge 7 differs from the signal variation from a ring 6. The way in which the measured wedge signals are compared with the measured ring signals follows from the signal amplitude frequency distribution (SDF=signal frequency distribution).

If the particles are spherical, the width of the frequency distribution depends on the number of particles in the cell (Poisson statistics) and on the non-uniform intensity distribution of the laser beam.

If the amplitude frequency distribution for ring signals is identical to the amplitude frequency distribution for the signals from a wedge-shaped section then SFD $(L_i^k)$=SFD $(L^k)$ and the particles concerned are spherical.

If the particles are not spherical and produce energy variations in the azimuth direction, the above equation is no longer valid.

Figure 5:
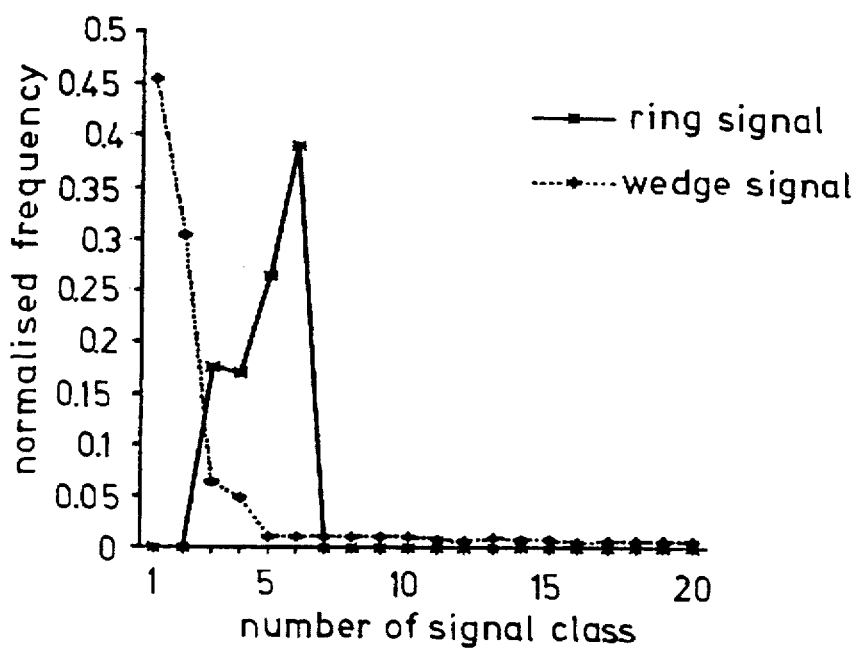
FIG. 5 is a plot of the signal amplitude frequency distribution in the case of a single fibrous particle and 200 readouts from the detector.
Figure 6:
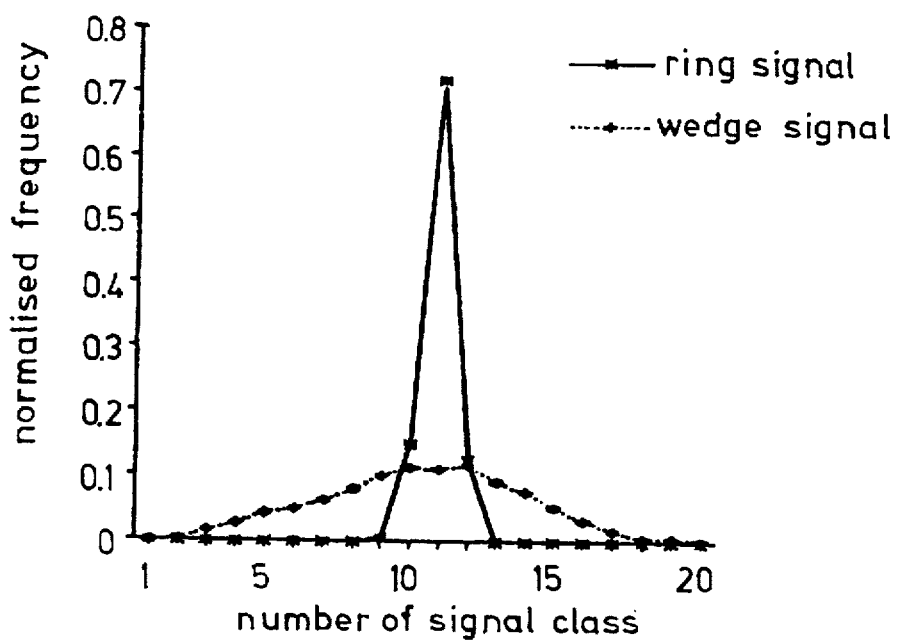
FIG. 6 presents a plot of the signal frequency distribution the case of 25 particles and 200 readouts from the detector.

FIGS. 5 and 6 show signal frequency distributions for signals originating from fibrous particles. When compiling this plot a Gaussian laser beam profile was assumed (see Optics Communication 90 (1992) 1–6. Comparison of the diffraction theory and the generalized Lorenz Mie theory for a sphere arbitrarily located into a laser beam; authors G. Grehan et al.).

A clear difference in signal frequency distribution is found to exist when the number of particles in the cell changes. A larger number of particles in the cell causes the median value of the distribution to shift towards higher signal values and the distribution becomes increasingly similar to a Gaussian distribution.

Figure 7:
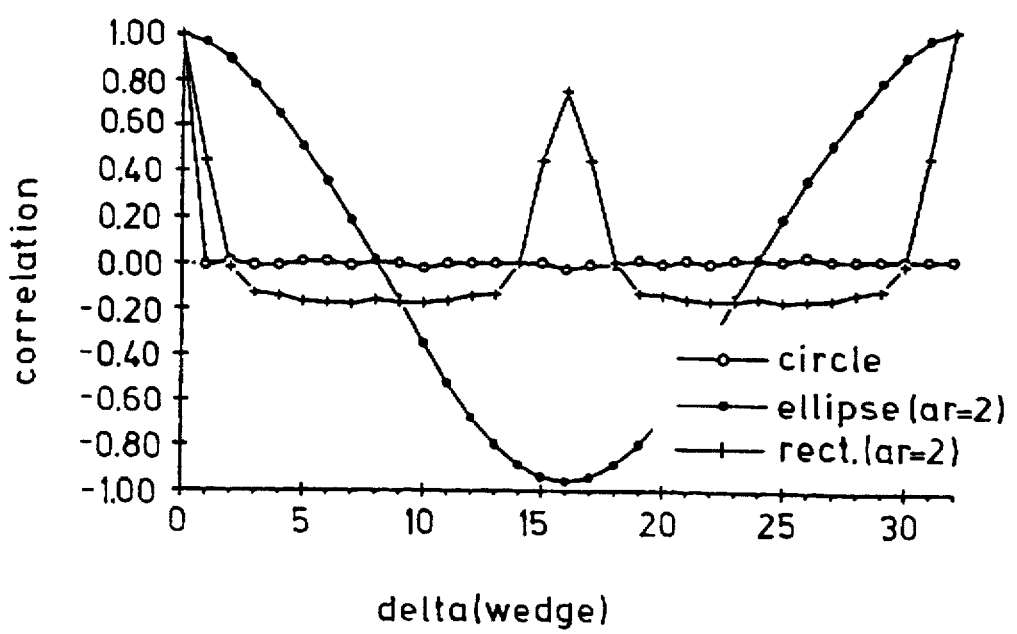
FIG. 7 shows a correlation plot for spherical. cube-shaped and ellipsoidal particles based on a simulation with 25 identical particles and 200 readouts.

FIG. 7 is a correlation plot for spherical, cube-shaped and ellipsoidal particles based on a simulation with 25 identical particle and 200 successive readouts. The signals from the outermost ring were used. The correlation calculation for signals on a ring subdivided into segments provide information on the actual average particle shape. A more detailed explanation is given in the article entitled "The use of Azimuthal Intensity Variations in Diffraction Patterns for Particle Shape Characterization" in the journal "Particle 8 Particle Systems Characterization". II (1994) pp. 194–199, published by VCH Verlagsgesellschaft mbH. Weinheim, Germany.

The features essential for the invention are that at least one segment is isolated on at least one ring and that the distribution of the amplitude frequency of the signals originating from the segment is compared with the distribution of the amplitude frequency of the signals originating from the ring in question.

If a ring is subdivided into several segments, calculation of the correlation between the signals from the segments provides accurate information on the average particle shape.

The shape-measuring apparatus can be made sensitive for a particle size range by subdividing all rings into wedge-shaped sections.

The determination of the shape of the particles is per se important for the determination of the particle size. The determination of the particle size will become more inaccurate if the particles have an elongated shape. By isolating one or more wedges (segments) on a ring it is possible, for each particle size determination, to establish whether the shape of the particles deviates substantially from the spherical. If this is the case, the particle size determination will be inaccurate.

Location of the cell 3 between the lens 4 and the detector 5 and adjustment of the size of the scattering pattern by moving the cell is not excluded. When a detector having a ring subdivided into wedges is used, an advantageous energy peak can be sought by changing the position of the cell.

A detector disc in which all rings are provided with an isolated segment and all segments are in a radial sequence is a possibility.

In place of a photo diode detector it is possible to use a polar Charged Coupled Device (CCD) array or a programmable mask in which both annular programmable light valves in the form of LCD's and wedge-shaped segments are incorporated.

I claim:

1. A method for determining the size and shape characteristics of particles, comprising the steps of directing a light beam onto a transparent cell containing particles flowing therein and measuring the intensity of the light scattered by the particles with a detector comprising plural concentric rings or parts of rings, at least one of which is provided with plural isolated segments, the rings and isolated segments being coupled to an energy meter, the signal amplitudes of which are statistically processed to give amplitude classes, and concurrently determining the size and shape characteristics of the particles from comparison of said amplitude classes.

2. The method according to claim 1, characterised in that the amplitude of the signals from one or more rings and the amplitude of the signals from one or more isolated segments are processed to produce an amplitude frequency distribution plot and the shape characteristics are determined from the difference in amplitude frequency distribution of signals originating from the ring or rings and signals originating from the isolated segment or isolated segments.

3. The method according to claim 1, characterised in that the amplitude of the signals from a number of isolated segments of one ring are processed to produce a correlation plot and the shape characteristics are determined from the shape of this plot.

4. An apparatus for determining the size and shape characteristics of particles, comprising a light source for generating a light beam, a transparent cell through which particles can be passed, a detector comprising plural rings which are coupled to an energy meter, and computing means for statistical processing of signal amplitudes to produce amplitude classes, wherein plural segments are isolated on at least one of the rings, said isolated segments being coupled to the energy meter, and wherein the computing means are adapted to process the amplitudes originating from the signals from the rings and the amplitudes originating from the signals from the isolated segments to produce the amplitude classes thereby concurrently to determine the size and shape characteristics of the particles.

5. The apparatus of claim 4, wherein said detector comprises one of a photodetector and a mask containing programmable light valves.

6. The apparatus of claim 4, each of said rings having a plurality of said segments.

7. A photodetector array comprising plural concentric rings or parts of rings adapted to be coupled to an energy meter, wherein plural segments are isolated on at least one of the rings or parts of rings, said segments also being adapted to be coupled to the energy meter thereby concurrently to determine the size and shape of particles that scatter light onto said array.

8. The photodetector of claim 7, further comprising a light source for generating a light beam, a transparent cell through which particles can be passed, and computing means for statistical processing of signal amplitudes to produce amplitude classes, wherein the computing means are adapted to process the amplitudes originating from the signals from the rings and the amplitudes originating from the signals from the isolated segments to produce the amplitude classes.

9. A mask comprising plural concentric programmable light valves in the form of rings or parts of rings, through which a light beam can be measured by a detector and which are coupled to an energy meter, wherein plural segments are isolated on at least one of the rings or parts of rings, and through which segments a light beam can be measured by a detector coupled to an energy meter thereby concurrently to determine the size and shape of particles that scatter light onto said light valves.

10. The mask of claim 6, further comprising a light source for generating a light beam, a transparent cell through which particles can be passed, and computing means for statistical processing of signal amplitudes to produce amplitude classes, wherein the computing means are adapted to process the amplitudes originating from the signals from the rings and the amplitudes originating from the signals from the isolated segments to produce the amplitude classes.

* * * * *